United States Patent [19]

Knepshield et al.

[11] Patent Number: 4,538,356
[45] Date of Patent: Sep. 3, 1985

[54] SURGICAL KNIFE WITH CONTROLLABLY EXTENDABLE BLADE AND GAUGE THEREFOR

[75] Inventors: William R. Knepshield; David D. Ogletree, both of Malvern; Nat Sander, Broomall, all of Pa.

[73] Assignee: KOI Associates, Inc., Frazer, Pa.

[21] Appl. No.: 676,316

[22] Filed: Nov. 29, 1984

Related U.S. Application Data

[62] Division of Ser. No. 410,476, Aug. 23, 1982, Pat. No. 4,499,898.

[51] Int. Cl.$^3$ .............................................. B27G 23/00
[52] U.S. Cl. ................................ 33/185 R; 33/180 R; 33/DIG. 8
[58] Field of Search ............. 33/180 R, 185 R, 169 R, 33/169 B, 169 F, DIG. 8

[56] References Cited

U.S. PATENT DOCUMENTS

| | | | |
|---|---|---|---|
| 3,315,368 | 4/1967 | Duby | 33/185 R |
| 3,323,221 | 6/1967 | Koch | 33/185 R |
| 3,423,837 | 1/1969 | Euverard | 33/169 F |
| 3,608,886 | 9/1971 | Greene | 33/180 R |
| 3,693,682 | 9/1972 | Hasfjord | 33/DIG. 8 |

Primary Examiner—Willis Little
Attorney, Agent, or Firm—Ratner & Prestia

[57] ABSTRACT

Surgical knife with controllably extendable blade, the blade retained by a blade holder extending through an axial opening in the knife body and connected with a member threadedly retained within the knife body for axial adjustment and also connected to an adjustment knob at the rear end of the knife. Another feature of the knife is a foot configuration which facilitates precise use and control of the knife. Preferably the invention also comprises the knife, as disclosed, in combination with a gauge for visually inspecting blade projection, the gauge indicator consisting of a pair of eccentric circles or portions thereof, the blade projection being measured by comparison with the radial distance between the two circles.

4 Claims, 11 Drawing Figures

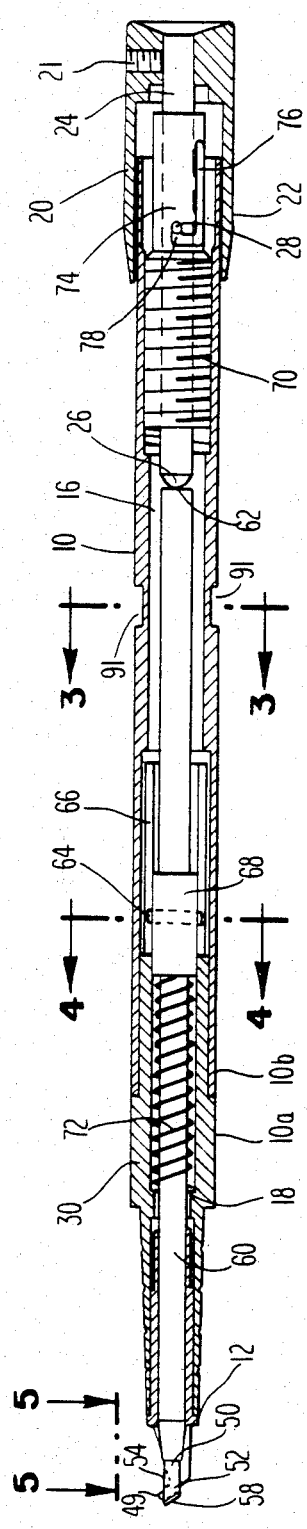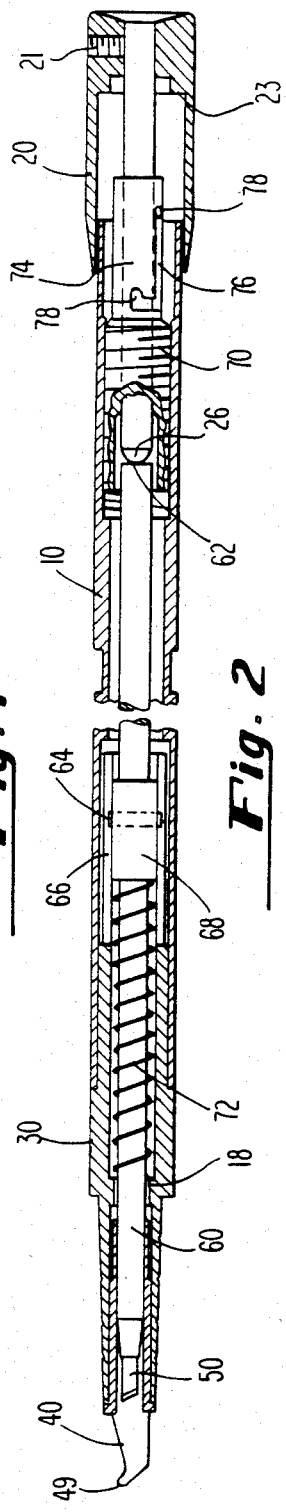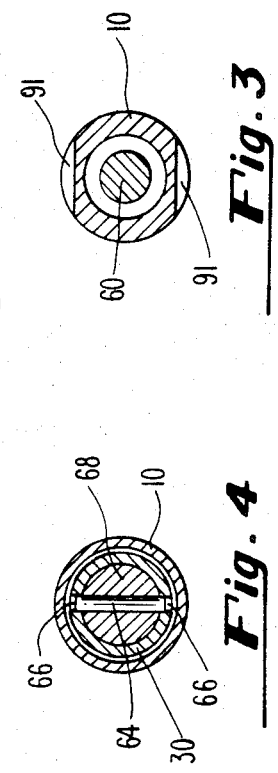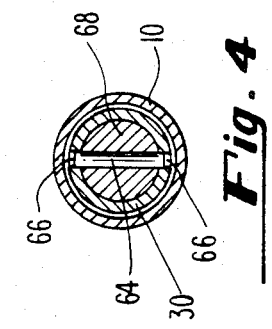

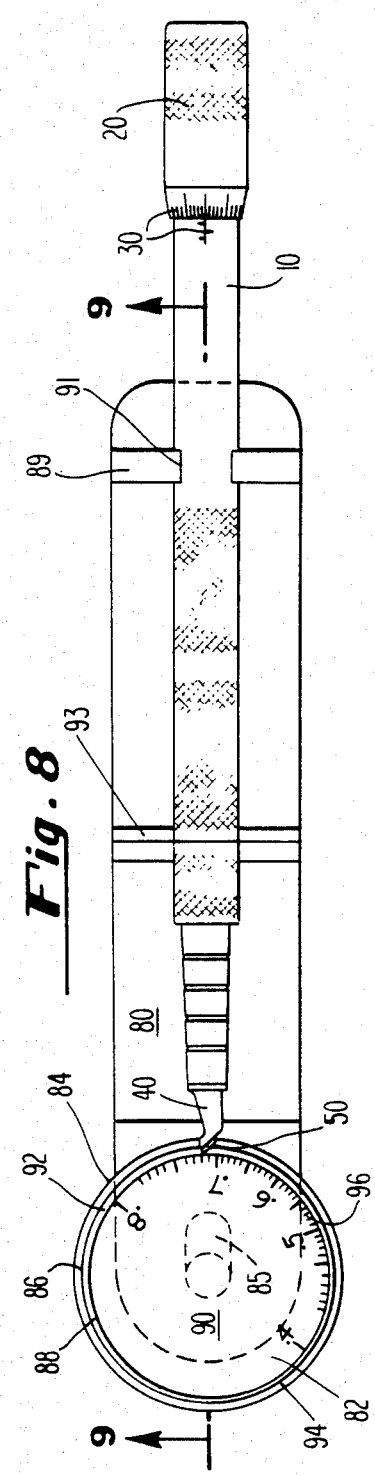
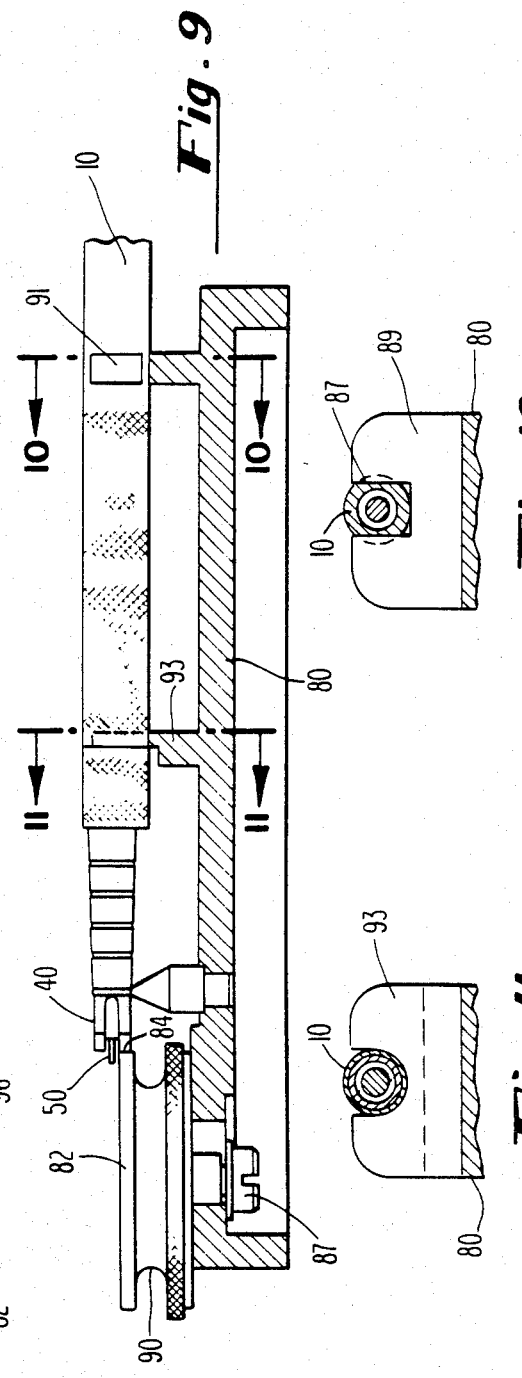
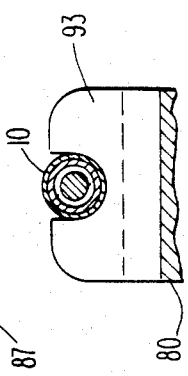

SURGICAL KNIFE WITH CONTROLLABLY EXTENDABLE BLADE AND GAUGE THEREFOR

This application is a division of application Ser. No. 410,476, filed 8/23/82, now U.S. Pat. No. 4,499,898.

INTRODUCTION

This invention pertains to a surgical knife with controllably extendable blade, particularly adapted for use in radial keratotomy, together with a gauge for visually measuring the blade extension of such a knife. In particular, this invention pertains to such a knife of improved design with respect to convenience in the adjustment of the controllably extendable blade and in the use of the knife for more precise placement and manipulation thereof.

In certain surgical procedures it is desirable to make an incision of a precisely controlled depth. In radial keratotomy, for example, an operation to which the present invention is particularly adapted, a plurality of radial incisions are made on the lens of an eye. It is important that the incision depth correspond to the lens thickness, and this has heretofore been accomplished by surgical knives, with diamond blades, in which the projection of the blade from a frontal surface of the knive is precisely adjusted and controlled to correspond to the desired incision depth. The frontal surface or bottom foot surface of the knife then is allowed to rest on the surface of the lens and the blade penetration and desired incision depth correspond to the length of blade projecting from the knife foot.

Such a knife heretofore sold in this country by Micra North America, Inc. is described in a one page flier, entitled "New Radial Keratotomy Diamond Knife", a copy of which is submitted with this application for purposes of examination. As seen in the Micra North America literature, this knife also includes a calibrated rear knob adjustment, by which the front projection of the blade from the frontal or foot surface is controlled. This knife further includes a bayonet extension and retraction means by which the blade may be retracted entirely within the knife body for protection when not in use. Moreover, the Micra North America knife includes a slot opening on either side of the blade and a "window" in that slot at the rear of the knife straddling the blade or plane of incision made by the blade, to facilitate better visual observation of the knife position.

Notwithstanding the state of the prior art with respect to surgical knives generally, and particularly with respect to such knives having features adapted for use in radial keratotomy, including that particularly disclosed in the Micra North America literature referred to above, there still remains a continuing need for a surgical knife improved with respect to convenience of use, controllable adjustment of the blade projection, foot locating and blade observation features, and a separate gauge for visually observing the blade projection from the knife.

The general object of the present invention is to provide such an improved surgical knife and particularly to provide a surgical knife peculiarly adapted for radial keratotomy by the inclusion of one or more design features to facilitate and ensure proper knife adjustment and to facilitate more precise control of the knife in use.

BRIEF DESCRIPTION OF THE INVENTION

This object is met, briefly, by a surgical knife and gauge, comprising a generally cylindrical knife body housing a retractable blade holder and blade projecting from the front end of the body and urged rearwardly against a cam member axially adjustable by a threaded positioning member connected to a rear adjustable knob through a cylindrical sleeve within the knife body; a bayonet connection is provided between the cylindrical sleeve and the cam member. The surgical knife of this invention further includes a foot member, i.e., a member surrounding the blade as it projects from the front end of the knife body, including an axial slot on either side of the flat blade member and relief cuts intersecting the blade slot so that the various edges of the blade are open to view by the knife user.

These relief cuts provide the user with an expanded view of several reference edges of the knife blade so as to enable precise placement and manipulation of the knife blade at almost any angle. Further, the knife foot includes a frontal resting foot surface, beyond which the blade projects, the resting surface being of relatively short length in the cutting direction so as to avoid "plowing" of the cutting surface while nevertheless providing precise depth positioning of the blade.

Calibrated marking on the rear adjustment knob and a mating outer surface of the knife body indicate the position of the blade relative to the blade body and thus the projection of the blade therefrom.

To assure correct blade projection, a separate visual gauge may also be used. Preferably, the surgical knife of this invention is used in combination with such a gauge and particularly includes locator means adapted to mate with corresponding positioning means in a gauge stand for that purpose. Preferably also, the knife is used with a gauge, which separately comprises another aspect of the present invention.

That gauge includes a gauge face with two offset circles or segments thereof, slightly spaced from one another and defining between them a continuously changing radial distance which, with proper indicator markings, is useful to measure the length of an element, by comparison to that radial distance.

For a better understanding of this invention, reference may be made to the detailed description of the preferred embodiment thereof which follows, taken together with the accompanying figures and the appended claims.

BRIEF DESCRIPTION OF THE FIGURES

In the figures,

FIG. 1 is a longitudinal sectional view of the surgical knife of the present invention, with the blade, blade holder, and bayonet retainer, in the forward or extended position;

FIG. 2 is a longitudinal cross-sectional view of the surgical knife of this invention differing from FIG. 1 in that the blade, blade holder, and bayonet retainer are in the retracted position;

FIGS. 3 and 4 are cross-sectional views of the surgical knife shown in FIG. 1, taken in the planes 3—3 and 4—4 respectively;

FIG. 8 is a top view of the gauge of the present invention assembled for use with the knife of the present invention, which is otherwise shown in FIGS. 1-7;

FIG. 9 is a longitudinal view, partially in section, of the gauge and knife, as shown in FIG. 8, taken in the plane 9—9 of FIG. 8;

FIGS. 10 and 11 are cross-sectional views of the knife and knife retaining means of the gauge shown in FIG. 9, taken in the planes 10—10 and 11—11 respectively of FIG. 9.

DETAILED DESCRIPTION OF THE INVENTION

Figure 5:
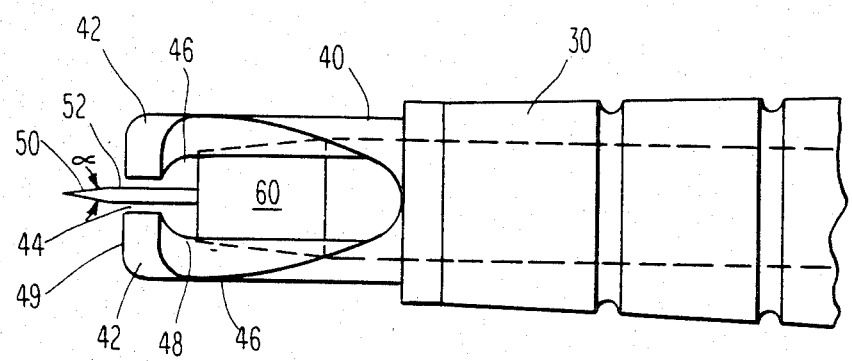
FIG. 5 is an enlarged detailed view of the blade, foot, and front portion of the body of the knife shown in FIG. 1, in the plane 5—5 of FIG. 1.

With reference specifically to FIGS. 1-4, there is shown a surgical knife, particularly adapted for use in radial keratotomy, and including a knife body 10, comprised for purposes of manufacture of a front body segment 10a and a rear body segment 10b. Body 10 otherwise includes front end 12 and rear end 14 and a centrally disposed axial opening 16 running therethrough, axial opening 16 also including a reduced diameter section 18 toward the front end thereof.

Figure 6:
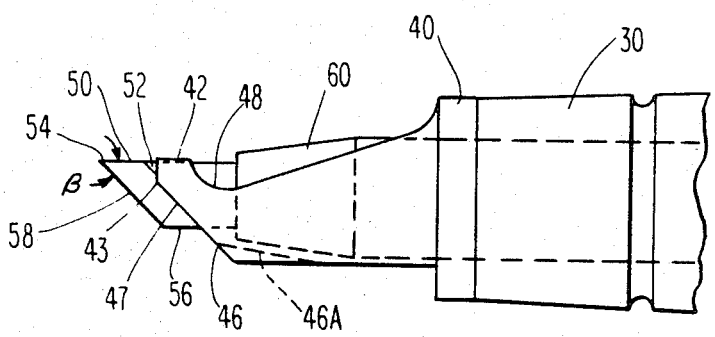
FIG. 6 is an enlarged detailed view similar to FIG. 5 but at a right angle thereto.

Blade 50, which projects from the front end of body 10, comprises flat side surfaces 52, trailing edge 54, leading edge 56, and cutting edge 58. Enclosed angle $\alpha$, between the two side surfaces of cutting edge 58 (as seen in FIG. 5), is generally on the order of 26°-45°, preferably 26°. Enclosed angle $\beta$, between trailing edge 54 and cutting edge 58 (as seen in FIG. 6), is generally on the order of 15°-45°, preferably 45°. Blade 50, in the forward position of the blade (as constrasted with the retracted position, to be described later and as illustrated in FIG. 2) projects forward of frontal surface 49 of knife foot 40, a predetermined and adjustably controlled length, generally within the range of 0.4-0.8 mm for radial keratotomy of humans. The positioning of blade 50 is maintained by its retention in blade holder 60, at the front end of which blade 50 is secured, and which otherwise extends rearwardly through axial opening 16 of body 10 to a cam surface 62 at the rear end thereof.

Preferably, radial alignment of blade 50 and blade holder 60 is maintained by one or more radial projections 64 matingly engaged in slots 66 on the inner surface of body 10. Still more preferably, axial alignment of blade holder 60 is maintained by an enlarged diameter section 68 thereof, slidingly engaged within the inner surface of axial opening 16 and body 10 and from which projects radial projection 64.

Blade 50 and blade holder 60 are urged rearwardly, preferably by compressed spring 72 trapped between enlarged diameter section 68 of holder 60 and reduced diameter section 18 of body axial opening 16.

Countering the rearward urging of spring 72, the rear cam surface 62 of blade holder 60 is urged forwardly by a cam member 24 having a front cam projection 26. Cam member 24 in turn urges blade holder forwardly by its retention through bayonet projection 28 in a bayonet slot 76, including short circumferential extensions 78 at the front and rear ends thereof. Bayonet slot 76 in turn is located in a rearwardly extending axial sleeve 74 of a blade positioner 70, threadedly retained within an internally threaded portion of body 10. Positioner 70 in turn is axially adjustable in its threaded retention within body 10 by rotation of adjustment knob 20 secured at the rear end of cam member 24, to which adjustment knob 20 is adjustably secured by two perpendicularly oriented set screws 21, in the preferred form of the present invention. Internal knob 20 also includes an abutment shoulder 23.

As seen in FIG. 8, calibration markings 30 at the front edge of an overlapping portion 22 of knob 20 and the mating outer surface of body 10 indicate the axial position of body 10, including foot 40 and frontal surface 49 thereof, relative to blade 50, retained by blade holder 60 and positioned through the connection of cam member 24 and threadedly retained positioner 70. (Dimension markings would ordinarily be associated with markings 30 but are not shown in FIG. 8.) Thus, rotational adjustment of knob 20 causes axial movement of threadedly adjustable positioner 70 and thus effects projection of blade 50 beyond frontal surface 49 of foot 40, associated with body 10.

Forward adjustment of the blade holder assembly is limited by contact of abutment 23 with the rear edge of body 10.

Typically, cutting edge 58 of blade 50 comprises a diamond particle cutting surface which is extremely sharp and vulnerable to misuse or abuse. Thus, when this surgical knife is not in use, blade 50 is desirably retracted within body 10, as shown in FIG. 2. In accordance with the preferred form of the present invention, this retraction movement is accommodated by the mating engagement of bayonet projection 78 and bayonet slot 76 with circumferential extensions 78 at the forward and rearward ends thereof. Extensions 78 each in turn include slight rearward axial extensions on their ends distal from the main slot 76 so that bayonet projection 28, for purposes of extension and retraction, is moved forward slightly by a forward movement of adjustment knob 20 and then circumferentially. This causes bayonet projection 28 to traverse the short circumferential extension 78 of slot 76. Then it is either urged rearwardly under the influence of spring 72, in the case of retraction, or urged forwardly by forward pressure on adjustment knob 20 by the operator, and it thus traverses the length of slot 76 to the opposing circumferential extension end slot 78 and into the short rearward axial extension at the distal end thereof. In this manner, the assembly of blade 50 and blade holder 60, together with cam member 24 and adjustment knob 20 is movable between two axially displaced positions. The rearward axial extensions of circumferential extensions 78 of bayonet slot 76 prevent further rearward movement of bayonet projection 28 at either position.

Alternatively, circumferential extensions 78 of slot 76 may be inclined to form an angle with radial planes of sleeve 74 (i.e., planes perpendicular to the axis thereof), the enclosed angles between slot 76 and extensions 78 being between 90° and 180°. Thus, such inclined extensions 78 provide a ramp whereby the primary axial activating projection and retraction forces on the blade holder assembly also move the bayonet projection along the angularly disposed slot end circumferential extensions to the distal end axially aligned locking slot extensions.

Figure 7:
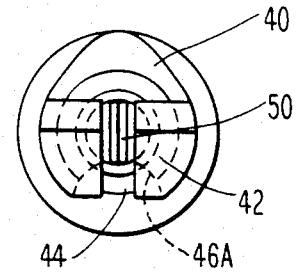
FIG. 7 is an end or front view of the knife shown in FIG. 1.

As indicated previously, use and control of the surgical knife of this invention is facilitated by the configuration of knife foot 40 which provides views of reference edges of blade 50 in complementary reference planes, as better seen in FIGS. 5 and 6. More specifically, in the view of FIG. 5, the two flat side surfaces of blade 50 are seen substantially in their entirety through slot opening 44 in an axial slot segment 42 of foot 40, just rear of frontal surface 49. Further, this view is enhanced by the expansion of slot 42 into the central axially aligned opening of a circular opening segment 46 of foot 40, at both the trailing edge 54 and leading edge 56 of blade 50. The former is provided by a cutaway section 48 of foot 40 as best seen in FIG. 6. The latter enhanced view expansion of slot 42 is provided by a truncated conical shape at the forward end of the axial central bore of foot 40, the essential shape of which is shown by hidden lines 46a in FIGS. 6 and 7.

As seen in the blade side plane profile of blade 50 and foot 40 of FIG. 6, cutaway portion 48 in foot 40, in the area of circular opening segment 46, provides both an outward expansion of the blade side opening visible in the plane of FIG. 5, and also a reference view of the trailing edge 54 of blade 50 rearwardly of frontal surface 49, and thus, with the knife in use, at a raised location above the incision surface.

The improved features of the foot member and the surgical knife of this invention also include a relatively short frontal surface 49, in the cutting direction of the knife, i.e., essentially the plane of blade 50, by virtue of its extension from a first line at or just forward of blade trailing edge 54 to a second line 43 just ahead of that edge. A second surface of foot 40 slopes rearwardly from second line 43, to reduce the area of contact between the surface of foot 40 in contact with the surface being cut, and thus to reduce or minimize the tendency to plow or raise that surface during the cutting operation.

Notwithstanding the convenient means provided in the surgical knife of this invention for the calibrated adjustment of the forward projection of blade 50 by the mechanism described above, a second means to assure proper blade projection is often desirable. Preferably, this comprises a visual comparison gauge. In accordance with the present invention, such a gauge is also provided in combination with a knife of this invention and further includes a gauge stand and gauge holding means, by which the knife is retained in a fixed position relative to the gauge indicator.

Preferably, the gauge provided, in accordance with the present invention, consists of (as seen in FIGS. 8-10) a gauge stand 80 with a flat disk indicator 82, having a cylindrical side surface 84 and a visual blade projection indicator consisting of a calibrated circumferential shape of variable width 92 at the edge of indicator 82. Calibrated circumferential shape 92 in turn is defined by two circles, one of which 86 comprises the outer circumference of flat disk indicator 82 and corresponds in shape to cylindrical side surface 84 thereof and the second of which 88 is eccentric thereto. Circumferential shape 92 in turn is provided with markings indicative of the radial distance between the respective circles 86 and 88. Disk indicator 82, together with cylindrical side surface 84 comprise a portion of gauge head 90, all of which is rotatable about the center of circles 86 and 88. Gauge head 90 is also axially adjustable in mounting slot 85, retained therein by a positioning screw 87. Thus, with the body of knife 10 supported on gauge stand 80 in supports 89 and 93, gauge head 90 is axially adjusted so that cylindrical side surface 84 abuts frontal surface 49 of foot 40 associated with body 10 of the surgical knife, while blade 50 is disposed just over (but preferably does not rest on) the flat disk indicator 82 and projects over a portion of the calibrated circumferential shape 92. The projection of blade 50 from frontal surface 49 is thus determined by rotationally adjusting disk indicator 82 until the blade projection length corresponds to the radial distance between circles 86 and 88, at which point the markings 96 thereon indicate the length of blade projection.

Alternatively, disk indicator 82 may comprise only segments of eccentric circle, rather than complete circles as shown. Such eccentric circle segments would, of course, define only a portion of circumferential shape 92, and this portion would include markings 96.

Preferably also, knife body 10 includes positioning means, by which the knife is retained at a particular position on gauge stand 10.

Most preferably, this comprises, as shown in conjunction with support 89, a pair of flat bottomed indentations 91, on opposite sides of body 10 at a particular axial position thereof, indentations 91 matingly engaging the sides of a U-shaped opening 87 in plate support 89. In this manner, body 10 is retained from both axial and radial displacement and the knife is particularly adapted for use in conjunction with a gauge of the type shown.

While this invention has been described with reference to a particular embodiment thereof, it should be understood that it is not limited thereto and the appended claims are intended to be construed to encompass not only the form and embodiment of the invention shown and described but to such other forms and embodiments, and obvious modifications thereof, as may be devised by those skilled in the art without departing from the true spirit and scope of this invention.

We claim:

1. Gauge for measuring the projection of a blade-like flat member from an elongated body associated therewith, said body having an axis along which said flat member projects and a front surface from which said member projects a distance to be measured, said gauge including a flat desk-like gauge indicator and a means for retaining said body in a fixed position with said flat member lying with a flat side thereof projecting over said gauge indicator, said gauge indicator having a cylindrical side surface, said front surface of said body abutting said side surface of said disk indicator when said body is retained in said fixed position, said gauge indicator further comprising a circular disk member, rotatable about the center point thereof, at least a portion of the edge of said member defining at least a portion of a first circle, and at least a portion of a second circle scribed on said disk member inward from said first circle and eccentric thereto, said circle portions defining at least a portion of a circumferential common shape of varying radial width, further including markings indicative of the radial distance between said circle portions at a multiplicity of circumferential points thereon.

2. Gauge, as recited in claim 1, including means for adjustably positioning said gauge indicator in a line parallel to said axis so as to bring said cylindrical side surface thereof into abutment with said front surface of said body.

3. Gauge, as recited in claim 1, wherein said body retention means includes at least two axially displaced supports, at least one of said supports being shaped to matingly engage a correspondingly shaped locating means on the outer surface of said body at a predetermined axial position thereof, said shaped support and locating means being adapted by mutual engagement thereof to retain said body in a predetermined axial and radial position.

4. Gauge, as recited in claim 3, wherein said locating means comprises a pair of flat bottomed indentations at a predetermined axial position on opposite sides of said body and said shaped support comprises a plate with a U-shaped cutout, in which is received said body, said plate, at the sides of said U-shaped cutout, fitting into said indentations.

* * * * *